US011154596B2

(12) United States Patent
Gurewich (10) Patent No.: US 11,154,596 B2
(45) Date of Patent: Oct. 26, 2021

(54) METHODS FOR THROMBOLYSIS (71) Applicant: Thrombolytic Science, LLC, Cambridge, MA (US)

(72) Inventor: Victor Gurewich, Cambridge, MA (US)

(73) Assignee: Thrombolytic Science, LLC, Cambridge, MA (US)

( * ) Notice: Subject to any disclaimer, the term of this patent is extended or adjusted under 35 U.S.C. 154(b) by 53 days.

(21) Appl. No.: 16/622,720

(22) PCT Filed: Jun. 15, 2018

(86) PCT No.: PCT/US2018/037855
§ 371 (c)(1),
(2) Date: Dec. 13, 2019

(87) PCT Pub. No.: WO2018/232305
PCT Pub. Date: Dec. 20, 2018

(65) Prior Publication Data
US 2021/0138046 A1 May 13, 2021

Related U.S. Application Data

(60) Provisional application No. 62/521,254, filed on Jun. 16, 2017.

(51) Int. Cl.
*A61K 38/49* (2006.01)
*A61P 7/02* (2006.01)
*A61K 9/00* (2006.01)
*A61K 45/06* (2006.01)

(52) U.S. Cl.
CPC ............ *A61K 38/49* (2013.01); *A61K 9/0019* (2013.01); *A61K 45/06* (2013.01); *A61P 7/02* (2018.01)

(58) Field of Classification Search
None
See application file for complete search history.

(56) References Cited

U.S. PATENT DOCUMENTS

| 4,381,346 A | 4/1983 | Syed |
| 5,055,295 A | 10/1991 | Welzel et al. |
| 5,108,901 A | 4/1992 | Anderson |
| 5,472,692 A | 12/1995 | Liu et al. |
| 5,510,330 A | 4/1996 | Martin et al. |
| 5,569,197 A | 10/1996 | Helmus et al. |
| 5,626,841 A | 5/1997 | Gurewich |
| 5,674,192 A | 10/1997 | Sahatjian et al. |
| 5,759,542 A | 6/1998 | Gurewich |
| 5,810,767 A | 9/1998 | Klein |
| 5,866,358 A | 2/1999 | Brandazza et al. |
| 6,364,893 B1 | 4/2002 | Shatjian et al. |
| 6,409,716 B1 | 6/2002 | Shatjian et al. |
| 6,699,230 B2 | 3/2004 | Jaafar et al. |
| 6,759,042 B2 | 7/2004 | Higazi |
| 7,070,958 B2 | 7/2006 | Sarmientos et al. |
| 7,074,401 B2 | 7/2006 | Gurewich et al. |
| 7,837,992 B2 | 11/2010 | Gurewich et al. |
| 8,187,592 B2 | 5/2012 | Gurewich et al. |
| 9,211,317 B2 | 12/2015 | Liu |
| 2002/0098179 A1 | 7/2002 | Brearley et al. |
| 2002/0138858 A1 | 9/2002 | Pinsky |
| 2005/0019863 A1 | 1/2005 | Sarmientos et al. |
| 2007/0148160 A1 | 6/2007 | Gurewich et al. |
| 2007/0298024 A1 | 12/2007 | Gurewich |
| 2009/0226413 A1* | 9/2009 | Gurewich ............ C12N 9/6462 424/94.64 |
| 2009/0286721 A1 | 11/2009 | Pan et al. |
| 2010/0196348 A1 | 8/2010 | Armstrong et al. |
| 2011/0081334 A1 | 4/2011 | Gurewich et al. |
| 2011/0229454 A1 | 9/2011 | Liu |
| 2013/0244941 A1 | 9/2013 | Mannesse et al. |
| 2018/0311322 A1* | 11/2018 | Gurewich .............. A61K 38/57 |

FOREIGN PATENT DOCUMENTS

| CA | 2426115 | 10/2004 |
| CN | 1377969 | 11/2002 |
| CN | 1142278 | 3/2004 |
| EP | 0 786 257 | 7/2003 |
| EP | 1 615 612 | 1/2011 |
| EP | 3215221 | 9/2017 |
| GB | 2197195 | 5/1988 |
| WO | 2016/073514 | 4/2011 |
| WO | WO 2016/073514 | 5/2016 |

OTHER PUBLICATIONS

Gurewich V. Why So Little Progress in Therapeutic Thrombolysis? J Thrombosis Thrombolysis 40(4)480-7, 2015. (Year: 2015).*
Gurewich V. Fibrinolytic Mechanisms of tPA, prouPA, Mutant prouPA and Their Implications for Therapeutic Thrombolysis. Cardiovacular Engineering and Technology 4(4)328-338, Dec. 2013. (Year: 2013).*
Gurewich V. Therapeutic Fibrinolysis J of the American College of Cardiology 68(19)2099-2106, 2016. (Year: 2016).*
Zarich, S et al. Sequential Combination Thrombolytic Therapy for Acute Myocardial Infarction. J of the American College of Cardiology 26(2)374-379, 1995. (Year: 1995).*
PCT International Preliminary Report on Patentability in International Appln. No. PCT/US2018/037855, dated Dec. 17, 2019, 8 pages.
BR Office Action in Brazilian Appln. No. BR112017008749-9. dated Jul. 8, 2020, 6 pages (with English translation).
EP Extended European Search Report in European Appln. No. 20158876.1, dated Jul. 24, 2020, 15 pages.
Patrick et al., "User-friendly algorithms for estimating completeness and diversity in randomized protein-encoding libraries," Protein Engineering, Jun. 1, 2003, 16(6):451-7.

(Continued)

*Primary Examiner* — Ralph J Gitomer
(74) *Attorney, Agent, or Firm* — Fish & Richardson P.C.

(57) ABSTRACT

Provided herein are methods for use in safe and effective thrombolysis, e.g., in therapy for a potential stroke or acute myocardial infarction ("AMI") at a maximum arterial patency rate with minimal associated hemorrhagic side effects.

20 Claims, 2 Drawing Sheets

(56) References Cited

OTHER PUBLICATIONS

Armstrong et al., "Fibrinolysis for acute myocardial infarction: the future is here and now," Circulation, May 27, 2003;107: 2533-2537.
Badylak et al., "Simple canine model of arterial thrombosis with endothelial injury suitable for investigation of thrombolytic agents," J. Pharmacological Methods, Jul. 1988; 19: 293-304.
Baglin et al., "Discovery and characterization of an antibody directed against exosite 1 of thrombin." J Thrommb Haemos, 2016;14:137-142.
Barnwell et al., "Safety and efficacy of delayed intraaterial urokinase therapy with mechanical clot disruption for thromboembolic stroke," Am J Neuroradiology, 1994;15(10):1817-1822.
Bennett et al., "Activation of the complement system by recombinant tissue plasminogen activator," J Amer Coll Cardiol., Sep. 1987;10: 627-632.
Braunwald, et al., "Announcement of protocol change in thrombolysis in myocardial infarction trial." J. Amer. Coll. Cardiol., 1987, 9(2):467.
Brooks et al., "CHARMM: A Program for Macromolecular Energy, Minimization, and Dynamics Calculations," J. Comp. Chem., 1983;4:187-217.
Bugge et al., "Urokinase-type plasminogen activator is effective in fibrin clearance in the absence of its receptor or tissue-type plasminogen activator," Proc Natl Acad Sci USA, 1996; 93:5899-5904.
Chen et al, Low-dose Tissue Plasminogen Activator is as Effective as Standard Tissue Plasminogen Activator Administration for the Treatment of Acute Ischemic Stroke. Current Neurovascular Research, 2014, 11, 62-67.
De Zwaan et al. "Continuous 48-h C1-inhibitor treatment, following reperfusion therapy, in patients with acute myocardial infarction" European Heart Journal, 2002;23:1670-1677.
Decision on Appeal in U.S. Appl. No. 11/447,455, dated Aug. 25, 2011, 13 pages.
Dmitry et al., "Rearrangements of the fibrin network and spatial distribution of fibrinolytic components during plasma clot lysis," J Biol Chem., 1996;271: 2133-2138.
EA Office Action in Eurasian Appln. No. 201790969, dated Oct. 2, 2018, 4 pages (with English translation).
Eissa et al, Optimizing the management of acute ischaemic stroke: a review of the utilization of intravenous recombinant tissue plasminogen activator (tPA). J Clin Pharnn Ther. Dec. 2012;37(6):620-9. Epub Jun. 19, 2012.
Eldering et al., "Expression of Functional Human C1 Inhibitor in COS Cells," The Journal of Biological Chemistry. 1988;263(24), Issue of Aug. 25:11776-11779.
Ellis et al., "Facilitated PCI in Patients with ST-Elevation Myocardial Infarction," New English Journal of Medicine, 358(21):2205-2217 (2008).
EP Office Action in European Appln. No. 15856204.1, dated Mar. 11, 2019, 3 pages.
European Search Report in European Patent Application No. 15856204.1, dated Jul. 6, 2018, 10 pages.
Fennerty et al., "Hemorrhagic complications of thrombolytic therapy in the treatment of myocardial infarction and venous thromboembolism," Chest., 1989;95: 88S-97S.
Final Office Action in U.S. Appl. No. 11/447,455, dated Apr. 22, 2008, 11 pages.
Final Office Action in U.S. Appl. No. 11/447,455, dated Aug. 6, 2009, 9 pages.
Final Office Action in U.S. Appl. No. 11/447,455. dated Jan. 28, 2009, 10 pages.
Final Office Action in U.S. Appl. No. 11/447,455, dated Mar. 15, 2010, 9 pages.
Grau et al. "Fibrinolytic activity of normal human blood monocytes," Thromb Res, 1989;53:145-162.
Gregorek et al. "Concentration sf C1 Inhibitor in Sera of Healthy Blood Donors as Studied by Immunoenzymatic Assay" Complement and Inflammation 8(5-6), 1991;310-312 (abstract).
Grossbard, "Genentech experience with rt-PA (activase)," J. Amer. Coll. Cardiol., 1987, 9(2):467.
Gulba et al., "Increased thrombin levels during thrombolytic therapy in acute myocardial infarction," Circulation, 1991, 83:937-944.
Gulba, et al., "Thrombin/antithrombin-III complex level as early predictor of reocclusion after successful thrombolysis," Lancet, 1988, 9(2):97.
Gurewich et al, Recombinant human C1-inhibitor prevents nonspecific proteolysis by mutant pro-urokinase during optimal fibrinolysis. Thromb Haemost 2009; 102: 279-286.
Gurewich et al., "Effective and Fibrin-specific Clot Lysis by a Zymogen Precursor Form of Urokinase (Pro-urokinase)", J. Clin. Invest. 1984;73:1731-1739.
Gurewich et al., "Synergism of tissue-type plasminogen activator (t-PA) and single-chain urokinase-type plasminogen activator (scu-PA) on clot lysis in vitro and a mechanism for this effect," Thromb Haemost, 1987;57:372-378.
Gurewich et al., "The selective uptake of high molecular weight urokinase-type plasminogen activator by human platelets," Fibrinolysis, 1995;9:188-195.
Gurewich et al., "Thrombolysis vs. bleeding from hemostatic sites by a prourokinase mutant compared with tissue plasminogen activator," J Thromb Haemost., Jul. 2006;4:1559-65.
Gurewich et al., New Therapeutic Agents in Thrombosis and Thrombolysis, 2nd edition, chap 36, "A mutant form of prourokinase that spares hemostatic fibrin," A.A. Sasaara and J. Loscalzo, eds., Marcel Dekker, Inc, NY, pp. 583-592, 2003, rec'd at the NIH Natl Library of Medicine, Bethesda, MD on Dec. 10, 2002.
Gurewich, "Therapeutic fibrinolysis. How efficacy and safety can be improved," J Am Coll Cardiol., 2016;68:2099-2106.
Gurewich, "Experiences With Pro-Urokinase and Potentiation of Its Fibrinolytic Effect by Urokinase and by Tissue Plasminogen Activator," Journal of the American College of Cardiology 10:16B-21B (1987).
Gurewich, "Coronary rethrombosis after successful thrombolysis," Circulation, 1993, 87:1759-1761.
Harpel et al., "Tissue plasminogen activator and urokinase mediate the binding of Glu-plasmninogen to plasma fibrin I. Evidence for new binding sites in plasmin-degraded fibrin I," J Biol Chem Apr. 10, 1985;260: 4432-4440.
Harris, "Second-Generation Plasminogen Activators," Protein Engineering, 1987;1(6):449-458.
Heckel et al., "Prediction of the three-dimensional structure of the enzymatic domain oft-PA" J. Cornn. Aided Mol. Des., 1988;2:7-14.
Hermann et al., "Facilitation of early percutaneous coronary intervention after reteplase with or without abciximab in acute myocardial infarction. Results from SPEED (GUSTO-4 pilot) trial," J Am Coll Cardiol, 36(5):1489-1496 (2000).
Hoylaerts et al., "Kinetics of the activation of plasminogen by human tissue plasminogen activator. Role of fibrin," J Biol Chem., Mar. 1982;257: 2912-2919.
Huisman et al., "On the role of C1-inhibitor as inhibitor of tissue-type plasminogen activator in human plasma." Thromb Haemost., Mar. 1995;73: 466-471.
International Preliminary Report on Patentability in International Application No. PCT/US2015/58878, dated May 9, 2017, 9 pages.
International Search Report and Written Opinion in International Application No. PCT/US2004/11840. dated Apr. 5, 2005, 9 pages [previously cited as: Notification of Transmittal of the International Search Report and Written Opinion of the International Searching Authority (and including the International Search Report and Written Opinion of the International Searching Authority) dated Apr. 5, 2005].
International Search Report and Written Opinion in International Application No. PCT/US2015/58878, dated Feb. 17, 2016, 10 pages.
JP Office Action in Japanese Appln. No. 2017-543288, dated Jun. 18, 2019, 6 pages (with English translation).
Kunkel, "Rapid and efficient site-specific mutagenesis without phenotype selection," Proc. Natl. Acad. Sci., Jan. 1985;82:488-492.
Lenich et al., "Thrombin Stimulation of Platelets Induces Plasminogen Activation Mediated by Endogenous Urokinase-Type Plasminogen Activator," Blood, 90:3579-86 (Nov. 1997).

(56) References Cited

OTHER PUBLICATIONS

Liu et al., "A transitional state of pro-urokinase which has a higher catalytic efficiency against glu-plasminogen than urokinase," J Biol Chem., 1992;767:15289-15792.
Liu et al., "A comparative study of the promotion of tissue plasminogen activator and pro-urokinase-induced plasminogen activation by fragments D and E-2 of fibrin," J Clin Invest., Dec. 1991;88: 2012-2017.
Liu et al., "A Site-Directed Mutagenesis of Pro-Urokinase at the Flexible Loop Region of Active Domain", Advances in Gene Technology: Protein Engineering and Beyond, Jan. 1, 1993, 6(Issue Supplment):45 (Abstract Only).
Liu et al., "A site-directed mutagenesis of pro-urokinase which substantially reduces its intrinsic activity" Biochemistry, Nov. 12, 1996;35: 14070-14076.
Liu et al., "Fragment E-2 from fibrin substantially enhances pro-urokinase-induced Glu-plasminogen activation. A kinetic study using the plasmin-resistant mutant pro-urokinase Ala-158-rpro-UK." Biochemistry, Jul. 14, 1992;31: 6311-6317.
Liu et al., "Inactivation of the Intrinsic Activity of Pro-urokinase by Diisoprophyl Fluorophosphate Is Reversible", The Journal of Biological Chemistry, vol. 210(15), na2es 8408-8410 (1995).
Liu et al.. "Prourokinase Mutant That Induces Highly Effective Cost Lysis Without Interfering With Hemostatsis", Circ Res. Apr. 19, 2002;90: 757-763.
Liu et al. "The Kinetics of Plasminogen Activation by Thrombin-Cleaved Pro-Urokinase and Promotion of its Activity bv Fibrin Fragment E-2 and by Tissue Plasminogen Activator." Blood, 81:980-987 (Feb. 1993).
Loscalzo et al., "Clot-Selective Coronary Thrombolysis with Pro-urokinase," Circulation, Apr. 1989, 79(4):776-782.
Mandel el al., "Calcium-dependent bacteriophage DNA infection," J. Mol. Biol., Oct. 14, 1970;53:159-162.
Meyer, "Randomised double-blind trial of recombinant pro-urokinase against streptokinase in acute myocardial infarction. PRIMI Trial Study Group," Lancet 1989;1:863-867.
Michels et al., "A double-blind multicenter comparison of the efficacy and safety of saruplase and urokinase in the treatment of acute myocardial infarction: Report of the SUTAMI study group," Thromb. Thrombolysis, 1995;2:117-124.
Montoney et al., "Comparison of the bleeding potential of vampire bat salivary plasminogen activator versus tissue plasminogen activator in an experimental rabbit model," Circulation, Mar. 1, 1995;91:1540-1544.
Murano et al., "The inhibition of high and low molecular weight urokinase in plasma," Blood, Mar. 1980;55: 430-436.
Nallamothu et al., "Time to Treatment in Primary Percutaneous Coronary Intervention." New England Journal of Medicine, 357(16):1631-1638 (2007).
NHLB Institute of the NIH, Symptoms of Myocardial Infarction. 2014b.
NHLB Institute of the NIH, Symptoms of Stroke. 2014a.
Nienaber et al., "Conformational Similarities between One-Chain and Two-Chain Tissue Plasminogen Activator (t-PA): Implications to the Activation Mechanism on One-Chain t-PA," Biochemistry, vol. 31, pp. 3852-3861 (1992).
Ning et al., "Prourokinase Mutant That Induces Highly Effective Clot Lysis Without Interfering With Hemostasis," Circulation Research, vol. 90 (7), pp. 757-763 (2002).
Non-Final Office Action in U.S. Appl. No. 11/447,455, dated Apr. 9, 2009, 7 pages.
Non-Final Office Action in U.S. Appl. No. 11/447,455, dated Aug. 1, 2008, 12 pages.
Non-Final Office Action in U.S. Appl. No. 11/447,455, dated Nov. 2, 2009, 8 pages.
Non-Final Office Action in U.S. Appl. No. 11/447,455, dated Nov. 30. 2011, 14 pages.
Orsini et al., "Efficient renaturation and fibrinolytic properties of prourokinase and a deletion mutant expressed in *Escherichia coli* as inclusion bodies", Eur. J. Biochem., vol. 195, pp. 691-697 (1991).

Owen et al., "Thrombolytic therapy with tissue plasminogen activator or streptokinase induces transient thrombin activity," Blood., Aug. 1988;72: 616-620.
Pannell et al., "A comparison of the rates of clot lysis in a plasma milieu induced by tissue plasminogen activator (t-PA) and rec-prourokinase: evidence that t-PA has a more restricted mode of action," Fibrinolysis, 1992;6:1-5.
Pannell et al., "Activation of Plasminogen bv Single-Chain Urokinase or by Two-chain Urokinase—A Demonstration That Single-Chain Urokinase Has a Low Catalytic Activity (Pro-Urokinase)", Blood., Jan. 1987;69:22-26.
Pannell et al., "Complementary modes of action of tissue-type plasminogen activator and pro-urokinase by which their synergistic effect on clot lysis may be explained," J Clin Invest., Mar. 1988;81: 853-859.
Pannell et al., "Pro-urokinase: a study of its stability in plasma and of a mechanism for its selective fibrinolytic effect," Blood., May 1, 1986;67:1215-1223.
Pannell et al., "Highly effective fibrinolysis by a sequential synergistic combination of mini-dose tPA plus low-dose mutant pro UK," PLOS One. 2015;10:1-15.
Pannell, "C1-inhibitor prevents non-specific plasminogen activation by a prourokinase mutant without impeding fibrin-specific fibrinolysis." J Thromb Haemost, 2007;5:1047-1054.
Parsons et al., "Diffusion- and perfusion-weighted MRI response to thrombolysis in stroke," Ann Neurol 51(1):28-37 (2001).
Petersen, "Kinetics of reciprocal pro-urokinase/plasminogen activation. Stimulation by a template formed by the urokinase receptor bound to poly (D-lysine)." Eur J Biochem, 1997;245:316-323.
Peterson et al., "Quenching of the Amidolytic Activity of One-Chain Tissue-Type Plasminogen Activator by Mutation ofLysine-416", Biochem, vol. 29, pp. 3451-3457 (1990).
Rao et al., "Thrombolysis in myocardial infarction (TIMI) trial—Phase I: Hemorrhagic manifestations and changes in plasma fibrinogen and the fibrinolytic system in patients treated with recombinant tissue plasminogen activator and streptokinase," J Amer Coll Cardiol., Jan. 1988;11:1-11.
Rapold et al., "Requirement of heparin for arterial and venous thrombolysis with recombinant tissue-type plasminogen activator," Blood, Mar. 1, 1991;77:1020-1024.
Rapold et al., "Plasma levels of plasminogen activator inhibitor type 1, beta-thromboglobulin, and fibrinopeptide A before, during, and after treatment of acute myocardial infarction with alteplase," Blood, 1991, 78(6):1490-1495.
Ross et al., "The effects of tissue plasminogen activator, streptokinase, or both on coronary-artery patency, ventricular function, and survival after acute myocardial infarction," N Engl J Med, 1993;329:1615-1622.
Singh et al., "Failure of thrombus to resolve in urokinase-tvpe plasminogen activator gene-knockout mice: rescue by normal bone marrow-derived cells." Circulation, 2003; 107:869-875.
Smith, "In vitro mutagenesis," Am. Rev. Genet, 1985;19:423-462.
Smith, "The influence of Bolus to Infusion Delays on Plasma Tissue Plasminogen Activator Levels," International Journal of Stroke, 9(7):939-942 (Oct. 2014).
Stone, "Facilitated angioplasty: paradise lost." The Lancet, 367:543-546 (2006).
Studier et al., "Use of bacteriophage T7 RNA polymerase to direct selective high-level expression of cloned genes," J. Mol. Biol., May 5, 1986;189:113-130.
Studier et al., "Use of T7 RNA polymerase to direct expression of cloned genes," Meth. Enzymol, 1990;185:60-89.
Suenson et al., "Initial plasmnin-degradation of fibrin as the basis of a positive feed-back mechanism in fibrinolysis," Eur J Biochem., 1984;140: 513-522.
Sun et al., "Identification of a flexible loop region (297-313) of urokinase-type plasminogen activator, which helps determine its catalytic activity," J Biol Chem., Sep. 19, 1997;272:23818-23823.
Swaim et al., "Fibringoen Assay," Clin. Chem., 13:1026-1028 (Nov. 1967).

(56) References Cited

OTHER PUBLICATIONS

Tebbe et al., "Randomized, double-blind study comparing saruplase with streptokinase therapy in acute myocardial infarction: the COMPASS equivalence trial.," J. Am. Coll. Cardiol., 1998;31:487-493.
Vaughan et al., "Urokinase binds to platelets through a specific saturable, low affinity mechanism." Fbrinolysis, 1990;4:141.
Verde et al., "Identification and primary sequence of an unspliced human urokinase poly(A)+ RNA", Proc. Natl. Acad. Sci., 1984;81:4727-4731.
Verheught, "Lyse now, stent later: the grace of GRACIA," Lancet, 364:1014-1015, 2004.
Verheugt, et al., "Reocclusion: the flip side of coronary thrombolysis," J. Amer. Coll. Cardiol., 1996, 27(4):766-773.
Voskuilen et al., "Fibrinogen lysine residue Aα157 plays a crucial role in the fibrin-induced acceleration of plasminogen activation, catalyzed by tissue-type plasminogen activator," J Biol Chem, 1987;262(13);5944-5946.
Wang et al., "Bovine chymotrypsinogen A X-ray crystal structure analysis and refinement of a new crystal form at 1.8 A resolution," J. Mol. Biol., 1985;185:595-624.
Weaver et al., "Prourokinase Study Group. New recombinant glycosylated prourokinase for treatment of patients with acute myocardial infarction," J. Am Coll. Cardiol., 1994;241: 242-1248.
Yuming et al., "High-level Expression and Purification of Human Pro-UK cDNA in *Escherichia coli*," Chinese Journal of Biotechnology, 1997;13(4):233-8.
Zarich et al, "Sequential Combination Thrombolytic Therapy for Acute Myocardial Infarction: Results of the Pro-Urokinase and t-PA Enhancement of Thrombolysis (PATENT) Trial." JACC vol. 26. No. 2 Aug. 1995:374-9.

CN Office Action in Chinese Appln. No. 201580058489.0, dated Jun. 9, 2020, 25 pages (with English translation).
IN Office Action in Indian Appln. No. 201747019519, dated Jul. 1, 2020, 6 pages.
MX Office Action in Mexican Appln. No. MX/a/2017/005793, dated Oct. 1, 2020, 9 pages (with English translation).
JP Office Action in Japanese Appln. No. 2017-543288, dated Apr. 14, 2020, 10 pages (with English translation).
CN Office Action in Chinese Appln. No. 201580058489.0, dated Dec. 2, 2020, 19 pages (with English translation).
International Search Report and Written Opinion dated Sep. 11, 2018 in international application No. PCT/US2018/037855, 14 pgs.
Collen et al., "Synergistic effect on thrombolysis of sequential infusion of tissue-type plasminogen activator (t-PA) single-chain urokinase-type plasminogen activator (scu-PA) and urokinase in the rabbit jugular vein thrombosis model," Thrombosis and Haemostasis, Oct. 1987, 58(07):943-6.
Hackett et al., "Effectiveness and safety of a single intravenous bolus injection of tissue-type plasminogen activator in acute myocardial infarction," The American Journal of Cardiology, Jun. 1, 1992, 69(17): 1393-8.
Robinson et al., "Latex D-dimer signal in in situ femoral vein thrombus in swine and effect of minidose exogenous tissue plasminogen activator bolus," Chest, Feb. 1, 2005, 127(2):622-9.
U.S. Final Office Action in U.S. Appl. No. 15/523,900, dated Jul. 29, 2020, 28 pages.
U.S. Final Office Action in U.S. Appl. No. 15/523,900, dated Sep. 25, 2019, 30 pages.
U.S. Non-Final Office Action in U.S. Appl. No. 15/523,900, dated Mar. 9, 2021, 23 pages.
U.S. Non-Final Office Action in U.S. Appl. No. 15/523,900, dated Feb. 28, 2019, 36 pages.
Verstraete et al., "Bolus alteplase," The Lancet, Oct. 21, 1989, 334(8669):989-90.

* cited by examiner

(▲) Sequential: 5 minute tPA exposure, wash, and incubation in plasma enriched with mprouPA
(▼) Simultaneous: incubation with tPA (0.2 µg/ ml) + mprouPA (6 µg/ ml)
(○) tPA (0.2 µg/ ml) alone
(●) mprouPA (6 µg/ ml) alone
(■) 5 minute tPA exposure, wash, and incubation in plasma
(✶) control – no activators

METHODS FOR THROMBOLYSIS

CLAIM OF PRIORITY

This application is a § 371 National Stage Application of PCT/US2018/037855, filed on Jun. 15, 2018, which claims the benefit of U.S. Provisional Application Ser. No. 62/521, 254 filed on Jun. 16, 2017. The entire contents of the foregoing application is incorporated herein by reference.

CLAIM OF PRIORITY

This application claims the benefit of U.S. Provisional Application Ser. No. 62/521,254 filed on Jun. 16, 2017. The entire contents of the foregoing application is incorporated herein by reference.

TECHNICAL FIELD

This invention relates to methods and compositions for safe and effective thrombolysis.

BACKGROUND

Thrombosis occurs when a blood clot (thrombus) forms inside a blood vessel and obstructs the flow of blood through the circulatory system. When a blood vessel is injured, the body uses platelets and fibrin to form a blood clot to seal injured vessels and prevent blood loss. This process is called hemostasis. Even when a blood vessel is not injured, blood clots may form in the body under certain circumstances. Blood clots consist largely of aggregated platelets and a mesh of cross-linked fibrin, which is a natural polymer of fibrinogen in the blood. When a thrombus is sufficiently large to reduce the blood flow to a tissue, hypoxia or anoxia can occur, leading to tissue damage or even tissue death. Depending on the location in the arterial system, i.e., heart, brain, or leg, a thrombus can trigger a heart attack (acute myocardial infarction (AMI)), stroke, or peripheral gangrene. In the venous circulation, the same process can cause thrombophlebitis (deep vein thrombosis (DVT)) or a pulmonary embolism. Together, these cardiovascular diseases constitute the leading causes of death and disability in industrialized countries.

Thrombolysis mainly involves the use of thrombolytic drugs to dissolve the disease-causing blood clot and restore blood flow. Thrombolytic drugs such as tissue plasminogen activator (tPA) and its derivatives in current use function by activating the proenzyme plasminogen to the protease plasmin, which degrades the fibrin mesh in the blood clot and makes the clot soluble, thus restoring blood flow through occluded blood vessels. However, the present thrombolytic drugs also induce degradation of hemostatic fibrin that seals wounds, and generate plasmin in plasma, which degrades three clotting factors: fibrinogen, Factor V, and Factor VII (hemophilic factor). Thus, current thrombolytic therapy carries the risk of causing bleeding from hemophilia-like side effects or from the degradation of hemostatic fibrin. This imposes serious limitations on the number of patients eligible for treatment and limits the dose of thrombolytic that can be used, thereby limiting efficacy. As a result, only about 5% of patients with stroke receive treatment and the efficacy of this treatment is limited.

Treating a stroke patient is tricky, because a stroke can be caused either by a blood clot or a bleeding vessel in the brain. However, properly diagnosing the specific cause of a stroke requires a CT scan or MRI, which can delay treatment if not immediately available. Absent such a proper diagnosis, it can be very dangerous to administer a clot-dissolving agent such as tPA if the cause happens to be a bleed rather than a blood clot, because the results of administering tPA or other thrombolytic agent to a patient whose stroke was caused by a brain bleed can be fatal.

SUMMARY

The present disclosure is based, at least in part, on the discovery of a paradoxical effect, which is that while tPA is required to initiate thrombolysis, the presence of tPA in the bloodstream thereafter inhibits the effectiveness of the other fibrin-specific activators, pro-urokinase and mutant pro-urokinase plasminogen activator (mproUK). Thus, if one administers a combination of two distinct thrombolytic agents, tPA and prourokinase, e.g., a mutant form of prourokinase (mproUK), in a particular order (the tPA must be administered first) and with a waiting period between the first and second administrations of at least two half-lives of tPA (e.g., at least 10 minutes) to allow a majority of the administered tPA to be cleared and/or inhibited by factors present in the blood (e.g., plasminogen activator inhibitor-1, PAI-1), then one can administer significantly smaller doses of the proUK mutant than previously found to be required and yet obtain an almost two-times higher rate of clot lysis with a two-fold lower percentage of fibrinogen degradation to achieve a maximum arterial patency rate with minimal associated hemorrhagic side effects. Therefore, thrombolysis using the new methods becomes almost twice as effective and half as likely to cause bleeding. This degree of efficacy with safety is not possible using any known activator alone or any combination or when administered together without the critical waiting period.

The mproUK can comprise a substitution of histidine for lysine at amino acid position 300 (Lys300→His) of pro-urokinase, referred to herein as "M5." mproUK, like proUK, is a proenzyme, i.e., the inactive precursor of the active enzyme. The mutant forms differ from proUK in that their enzymatic form is mutant urokinase or mUK, which unlike urokinase (UK), is inhibited by a plasma inhibitor, C1-inhibitor, which additionally to the lower doses necessary, helps to reduce the bleeding side effects seen with proUK, which are due to UK, and for which there is insufficient inhibitor PAI-1 in the plasma.

For patients with stroke or AMI, the time needed for thrombolysis and reperfusion is critical to clinical outcome and survival rate. This means that treatment must be safe enough to be given outside the hospital without time-consuming preliminary diagnostic testing. However, this is possible only if the hemorrhagic risk is greatly reduced or eliminated, as is the case with the new methods described herein including the administration of a mini-dose of tPA (e.g., a bolus of less than 5.0 mg, e.g., less than or equal to 4.5 mg, 4.0 mg, 3.5 mg, 3.0 mg, 2.5 mg, or 2.0 mg) and mini-dose of proUK, e.g., mproUK (e.g., an infusion over 45 to 90 minutes (e.g., 45, 50, 55, 60, 65 70, 80, or 90 minutes) at a rate of 20 to 50 mg/hour, e.g., 20 to 40 mg/hour, e.g., 25, 30, 35, 40, or 45 mg/hour) in sequence, with a minimum waiting period of at least ten minutes between the two administrations.

If the endogenous concentration of C1-inhibitor is insufficient in a given subject, it can be supplemented in the new methods by administering an effective amount of a C1-inhibitor, e.g., a commercially available C1-inhibitor such as CINRYZE®, CETOR®, BERINERT®, and RUCONEST®. The C1-inhibitor is an additional precaution to inhibit the conversion of mproUK to mutant UK in plasma, but may not be necessary due to the low dose of mproUK required and the fact that C1-inhibitor is an acute phase reactant, which is automatically elevated by the body after events like heart attack or stroke.

In a first aspect, this disclosure provides methods of treating a subject with symptoms of a stroke or an acute myocardial infarction (AMI) at a maximum arterial patency rate with minimal associated hemorrhagic side effects, the method including (a) identifying a subject who potentially had a stroke or AMI by observing one or more symptoms of a stroke or AMI without taking time to determine the cause of the stroke or AMI (e.g., by observing one or more symptoms of a stroke or AMI, without taking the time for radiological or other diagnostic confirmation prior to administering any medication); (b) administering to the subject a mini-dose, e.g., a mini-bolus, of less than 5 mg of tissue plasminogen activator (tPA), e.g., 2.0, 2.5, 3.0, 3.5, 4.0, or 4.5 mg of tPA; (c) waiting at least ten minutes, e.g., 11, 12, 13, 14, 15, 16, 17, 18, 19, 20, 21, 22, 23, 24, 25, 26, 27, 28, 29, or 30 minutes, after completing the administration of the tPA; and (d) thereafter administering an intravenous infusion of a mini-dose of pro-urokinase (proUK), e.g., mutant proUK (mproUK) or native proUK, infused over 45 to 90 minutes, e.g., 45, 50, 55, 60, 65, 70, 75, 80, 85, or 90 minutes, at a dosage rate of 20 to 50 mg/hour, e.g., 20 to 40 mg/hour, e.g., 25, 30, 35, 40, or 45 mg/hour; wherein a maximum arterial patency is achieved with minimal associated hemorrhagic side effects.

For example, in some implementations, the mini-dose of tPA is a bolus of 2.0 to 4.5, 2.0, 2.5, 3.0, 3.5, or 4.0 mg of tPA. The proUK can be mutant proUK (mproUK), e.g., an mproUK with a substitution of histidine for lysine at amino acid position 300 (Lys300→His) of native proUK.

In some embodiments, the subject has symptoms of a stroke. In some embodiments, wherein the minimal associated hemorrhagic side effects are determined as a level of fibrinogen degradation in the subject's blood of less than about 30 percent. In certain embodiments, the maximum arterial patency rate is indicated as having been achieved by a Thrombolysis In Myocardial Infarction (TIMI) score of 3.

In some implementations, the proUK is administered as an intravenous infusion at a rate of 20-40 mg/hour for 45-90 minutes, e.g., an intravenous infusion at a rate of 20-30 mg/hour for 45-60 minutes. In some embodiments, the methods further include administering to the subject a bolus of C1-inhibitor, e.g., before or at about the same time as the administration of the proUK. For example, the C1-inhibitor can be administered in an amount sufficient to establish a concentration of C1-inhibitor that is about 500-750 µg/ml in the subject's blood. For example, the C1-inhibitor can be administered as a bolus of 500-1500 mg of C1-inhibitor.

In another aspect, the disclosure provides kits including a first composition in a first container (e.g., a syringe or glass or plastic vial) comprising 2-5 mg, e.g., 2.0, 2.5, 3.0, 3.5, 4.0, 4.5 mg, of tissue plasminogen activator (tPA) formulated for administration as a bolus; and a second composition in a second container comprising 20-50 mg, e.g., 20-40 mg, 20-30 mg, 20 mg, 25 mg, 30 mg, 35 mg, or 40 mg, of a pro-urokinase (proUK), e.g., native proUK or a mutant proUK, e.g., comprising a substitution of histidine for lysine at amino acid position 300 (Lys300→His) of native pro-UK, formulated for intravenous infusion for 45-90 minutes, e.g., 45, 50, 55, 60, 65, 70, 75, 80, 85, or 90 minutes, after a waiting period of at least ten minutes after administration of the tPA.

In some implementations, the kits can further include 500-1500 mg, e.g., 600, 700, 800, 900, 1000, 1100, 1200, 1300, 1400, or 1500 mg, of C1-inhibitor formulated for administration as a bolus.

In some embodiments, the kit includes 4.0 mg of tPA formulated for a bolus injection and 40 mg of mproUK formulated for an infusion for one hour.

In another general aspect, the disclosure provides compositions for use in any of the methods described herein, e.g., treating a subject with symptoms of a stroke or acute myocardial infarction (AMI) at a maximum arterial patency rate with minimal associated hemorrhagic side effects, the composition including a first composition including less than 5 mg, e.g., 2.0, 2.5, 3.0, 3.5, 4.0, 4.5 mg, of tissue plasminogen activator (tPA), wherein the first composition is ready to be, or can be prepared to be, administered to a subject in a dosage regime of a bolus; and a second composition comprising a pro-urokinase (proUK), e.g., a native proUK or a mutant proUK (mproUK), wherein the second composition is ready to be, or can be prepared to be, administered to a subject by an intravenous infusion at a dosage of 20 to 50 mg/hour, e.g., 20-30 mg, 20 mg, 25 mg, 30 mg, 35 mg, or 40 mg, for 45 to 90 minutes, e.g., 45, 50, 55, 60, 65, 70, 75, 80, 85, or 90 minutes, following at wait period of at least ten minutes after the administration of the first composition; wherein the subject is identified as potentially having had a stroke or AMI by observing one or more symptoms of a stroke or AMI without taking time to determine the cause of the stroke or AMI prior to administering the first composition; and wherein a maximum arterial patency is achieved with minimal associated hemorrhagic side effects.

In some implementations, the minimal associated hemorrhagic side effects are determined as a level of fibrinogen degradation in the subject's blood of less than about 30 percent. In some implementations, the maximum arterial patency rate is indicated as having been achieved by a Thrombolysis In Myocardial Infarction (TIMI) score of 3.

In some implementations, the proUK is a proUK mutant has a substitution of histidine for lysine at amino acid position 300 (Lys300→His) of native pro-urokinase.

In some embodiments, the proUK is ready to be, or can be prepared to be, administered as an intravenous infusion of the proUK at a rate of 20-40 mg/hour for 45-90 minutes.

In certain implementations, the composition can further include a third composition including a bolus of C1-inhibitor, e.g., a bolus of 500-1500 mg of C1-inhibitor.

In some embodiments of these methods, kits, and compositions, the minimal risk of associated hemorrhagic side effects can be determined from an associated dotting factor like fibrinogen degradation in the subject's blood of less than about 30 percent, e.g., less than 27.5%, 25%, 22.5%, or 20% fibrinogen degradation (whereas fibrinogen degradation is about 50 to 80% with monotherapy by either tPA, proUK, or mproUK alone). In some embodiments, the maximum clot lysis rate is indicated as having been achieved by a Thrombolysis In Myocardial Infarction (TIMI)-3 patency rate. In other embodiments, the maximum clot lysis rate is indicated in vivo as having been achieved by a TIMI-3 coronary patency rate of more than 60% at 24 h (it is 45% for tPA), or an onset of reperfusion within 75 minutes, e.g., within 70, 60, 50, 40, or 30 minutes.

In some embodiments, the tPA and the mproUK in sequence lyse 50% of a mass of at least one blood clot in the subject in less than one hour. In some of these methods, the tPA and the mproUK together lyse the blood clots in the presence of the C1-inhibitor with less than 30% fibrinogen degradation when compared to monotherapy by either tPA or mproUK alone where it is over 50% at an equivalent clot lysis rate.

The term "treatment" or "therapeutic treatment" means the administration of one or more pharmaceutical agents to a subject or the performance of a medical procedure on the body of a subject. The term therapeutic treatment also includes an adjustment (e.g., increase or decrease) in the dose or frequency of one or more pharmaceutical agents that a subject can be taking, the administration of one or more new pharmaceutical agents to the subject, or the removal of one or more pharmaceutical agents from the subject's treatment plan.

As used herein, a "subject" or "patient" is a human.

An "effective amount" used herein is an amount sufficient to achieve thrombolysis without causing significant hemorrhagic or hematological hemophilia-like side effects. An effective amount can be administered in one or more administrations, applications, or dosages. A therapeutically effective amount of a pharmaceutical composition (i.e., an effective dosage) depends on the pharmaceutical composition selected.

The "a maximum arterial patency rate" is defined herein as a rate of lysis of blood clots in a patient to achieve a TIMI-3 patency rate faster than can be achieved by monotherapy with tPA, proUK, or mproUK at fibrin-specific doses (i.e., a dose of the drug at which no faster clot lysis can be achieved by adding additional drug, e.g., a plateau in the clot lysis rate is shown at the maximally effective dosage) and with greater specificity, i.e., a lower rate of degradation of clotting factors, fibrinogen, V, VII, and VIII, which is the cause of hemorrhagic side effects. It is important to note that the maximum non-fibrin-specific lysis rate and arterial patency rate achieved using monotherapy, e.g., with tPA or M5, would cause an unacceptable incidence of bleeding and, therefore, these doses have never been used clinically. Surprisingly, the present therapeutic methods achieve the higher arterial patency rate than heretofore possible without hemorrhagic side effects, due to the higher specificity and lower degree (less than 30%) of fibrinogen degradation.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The present disclosure is based, at least in part, on the discovery that thrombolysis can be achieved at a maximum arterial patency rate so as to achieve more rapid reperfusion of obstructed arteries, e.g., at a Thrombolysis In Myocardial Infarction (TIMI)—3 patency rate, within about 60-75 minutes and with minimal associated hemorrhagic side effects. The new methods include first administering a mini-dose of tissue plasminogen activator (tPA) as an intravenous bolus, then waiting for at least 10 minutes, and thereafter administering a mini-dose of pro-urokinase (proUK), for example, a mutant proUK (mproUK) such as one that comprises a substitution of histidine for lysine at amino acid position 300 (Lys300→His) of pro-urokinase, referred to herein as "M5." The applicant has discovered that this extra step of a minimum waiting period for the administered tPA to be cleared from the circulation avoids significant interference by tPA of effective thrombolysis by mproUK, thereby reducing the required dosage of proUK by about half. Thus, the waiting period significantly improves prior methods of dual administration of tPA and proUK or mproUK, while at the same time reducing the risk of side effects.

For patients with stroke or acute myocardial infarction, the time needed for reperfusion by thrombolysis, which is the only means by which it can be done rapidly, is critical to clinical outcome and survival rate. However, to make this possible, treatment must also be safe enough so that patients can be treated before time-consuming diagnostic tests, which usually require hospitalization. Provided herein are methods of treating a subject who potentially had a stroke or acute myocardial infarction. A key aspect of the new methods is the waiting period of at least two half-lives of tPA, e.g., at least ten minutes, after the tPA has been administered, so that the administered tPA can cleared and/or inhibited by plasma inhibitors normally found in the blood stream.

These methods can be used to treat patients with symptoms of stroke or acute myocardial infarction without the delay caused by time-consuming diagnostic procedures, thereby enhancing the chances of better clinical outcome and survival rate for those patients. Since fibrinolysis can be achieved as shown herein for the first time with such low "mini-doses" of tPA and "mini-doses" of mproUK in the sequential combination, non-specific activation of plasminogen and the hemophiliac-like side effects associated with higher doses of plasminogen activator regimens is reduced to a minimum level while still achieving a faster maximum arterial patency rate than heretofore possible, i.e., a TIMI-3 patency rate, which is higher than that of monotherapy with any activators or combination therapy with previous dosing and administration regimens lacking a waiting period of at least ten minutes. This is achieved with a lower risk of bleeding due to the lower doses required. This is achieved in part by allowing the tPA to be eliminated or inhibited before the mproUK is administered. The reason is due to the finding that the presence of tPA in plasma acts as a competitive inhibitor of mproUK thereby interfering with lysis. Also provided herein are kits that include a first composition comprising tPA and a second composition comprising mproUK, for use in the methods described herein.

The present inventor has discovered that fibrinolysis can be attained with a sequential combination of a mini-dose of tPA (only 2-5% of the standard 100 mg dose) plus a mini-dose of a mproUK, e.g., M5 (only 30-40% of the monotherapy dose), which induces a maximum arterial patency rate, e.g., TIMI-3 patency rate, with a minimal percent of fibrinogen degradation of less than about 30% (e.g., about 20-25%). This tPA-mproUK sequential combination, with a minimum waiting period of at least ten minutes between administrations, achieves fibrinolysis at a lysis rate that is greater than that possible by monotherapy with any known plasminogen activator, including either tPA or mproUK. This is also a rate that cannot be achieved with any activator combination, in the absence of the waiting period, without an unacceptable bleeding risk. Thus, the methods described herein provide thrombolysis that is clearly superior to any earlier alleged synergistic combination, which would not include the newly discovered dual benefits of a maximum blood clot lysis rate and maximum arterial patency rate with a minimum bleeding risk for the patient, i.e., this is possible by the sequential combination only when it includes the key step of the minimal waiting period of at least ten minutes, which allows sufficient time for tPA to be eliminated from blood so it does not interfere with lysis by mproUK.

The "maximum arterial patency rate" is defined herein as a rate of lysis of blood clots in a patient that is faster than that achievable with monotherapy with tPA, proUK or mproUK at clinically acceptable doses (in vitro it is the maximum rate of fibrinolysis that can be achieved without extensive (meaning >50%) fibrinogenolysis. However, it is important to note that the maximum arterial patency rate achievable using monotherapy, e.g., with tPA or M5, would cause significant bleeding in a patient, as indicated, for example, by a level of fibrinogen degradation of greater than 50%. The "maximum efficacy and safety" achieved by the new methods described herein is defined as a higher than otherwise possible fibrinolysis rate accompanied by a lower than previously attainable risk of bleeding.

For example, the tPA-mproUK sequential combination with the minimum waiting period can induce fibrin-specific clot lysis, and as a result blood vessel patency, more rapidly than monotherapy with any known activator or that with any combination in the absence of the waiting period between tPA and proUK or mproUK. The combination with the waiting period also allows significantly lower doses of mproUK than with earlier combination therapies, since mproUK is thereby freed from inhibition, and thus the new methods are far more fibrin-specific, safer, and economical.

Clinically, the tPA-mproUK sequential combination therapy with the minimum waiting period of at least ten minutes can be used to treat patients with stroke or heart attack symptoms without the delay caused by time-consuming diagnostic procedures, which are currently mandatory due to the significant bleeding risk associated with tPA monotherapy. Treatment can be administered on suspicion or in the ambulance and the sequential combination therapy offers superior efficacy, and better safety and clinical benefit than tPA monotherapy, which is the only thrombolytic agent currently approved and available.

The maximum arterial patency rate of the present methods in vivo can be determined, for example, by standard techniques for assessing blood vessel recanalization. The grade of blood vessel occlusion can be assessed by the Thrombolysis In Myocardial Infarction (TIMI) score, wherein a TIMI score of 0 is complete occlusion, TIMI of 1 is minimal perfusion, TIMI of 2 is partial flow (recanalization), and a TIMI score of 3 is complete flow. The TIMI study group developed this grading scale for coronary blood flow based on visual assessment of the rate of contrast opacification of the infarct artery (see, e.g., The TIMI Study Group. The Thrombolysis in Myocardial Infarction (TIMI) trial: phase I findings. N. Engl. J. Med. 1984; 33:523-530; and The TIMI Study Group. Comparison of invasive and conservative strategies after treatment with intravenous tissue plasminogen activator in acute myocardial infarction: results of the Thrombolysis in Myocardial Infarction (TIMI) phase II trial. N. Engl J. Med., 1989, 320:618-627, which are incorporated herein by reference for their description of the TIMI grading scale).

The TIMI flow grade has become the standard for semi-quantitative evaluation of myocardial perfusion before and after coronary reperfusion therapies as well as for determining therapies for stroke. Both TIMI flow grades 2 and 3 are considered indicative of successful reperfusion, though TIMI-3 correlates best with mortality reduction. Thus, as used herein, a maximum arterial patency rate is associated in human subjects or patients with achieving a TIMI score of 2 or 3, but preferably 3, within about 75 minutes or less, e.g., within 70, 65, 60, 55, 50, 45, 40, 35, or 30 minutes.

Tissue Plasminogen Activator

Tissue plasminogen activator (tPA) is a serine protease stored in endothelial cells lining the blood vessel wall. When a thrombus occludes a blood vessel, tPA is released from the blood vessel wall and lyses fibrin clots.

Currently most therapeutic thrombolysis is performed using tPA and its derivatives, however, tPA can cause hemorrhagic side effects. For example, tPA at a dose of 150 mg has been shown to induce superior coronary thrombolysis, but has been accompanied by an unacceptable incidence of intracranial hemorrhage, obliging the adoption of a less effective dose of 100 mg (Braunwald, J. Amer. Coll. Cardiol., 9: 467, 1987; Grossbard, Amer. Coll. Cardiol., 9:467, 1987). In comparative clinical trials in acute myocardial infarction (AMI) patients, results with percutaneous coronary intervention (PCI) were significantly better than intravenous administration of tPA, although PCI is more costly, technically demanding, and time-consuming. This clinical outcome was surprising, but can be explained by the following tPA properties: (1) the therapeutic dose of tPA is limited by the intracranial hemorrhage complications; and (2) tPA's efficacy is undermined by a relatively high coronary rethrombosis rate, which is associated with hematological evidence of thrombin generation (Verheugt, J. Am. Coll. Cardiol., 1996, 27: 766-773; Gurewich, Circulation. 1993, 87: 1759-1761; Rapold, Blood, 1991, 78:1490-1495; Gulba, Lancet. 1988, 2: 97; Gulba, Circulation. 1991, 83: 937-944).

In ischemic stroke, a further dose reduction was required due to a 20% incidence of intracranial hemorrhage complications when administering tPA at doses equivalent to those used in AMI (Hacke, JAMA, 1995, 274: 1017-1025). The use of heparin, which is used with tPA in AMI is precluded in stroke. The heparin is used to overcome tPA's reocclusion rates of 14-31% (Alexandrov, Neurology, 2002, 59: 862-867; Rubiera, Stroke, 2005, 36: 1452-1456; Saqqur, Stroke, 2007; 38: 69-74). The net result has been that only about 2-5% of patients with ischemic stroke are treated with tPA in the United States (Kleindorfer, Stroke, 2008; 39: 924-928). It is noteworthy that proUK was free of this reocclusion risk.

In AMI, the treatment of choice is no longer tPA but PCI, despite the several hour treatment delay required by hospitalization and entry into a catheterization unit.

tPA-induced bleeding is believed to be primarily related to lysis of hemostatic fibrin needed for repair of wear-and-tear injury sites in the vessel wall, which are occult and unpredictable. This risk is tPA dose-dependent and is increased when tPA is administered by a prolonged infusion, as in monotherapy rather than as a mini-bolus. proUK/M5 spares these hemostatic sites due to its not having this fibrin-binding property or any fibrin affinity.

Pro-Urokinase and Pro-Urokinase Mutants

Pro-urokinase (proUK) is not as well-known as a thrombolytic drug as tPA, but Phase 3 clinical studies in AMI have been completed (Michels, J. Thromb. Thrombolysis, 1995, 2: 117-124; PRIMI Trial Study Group. Lancet 1989, 1: 863-867; Tebbe, J. Am. Coll. Cardiol., 1998, 31: 487-493). ProUK induced little (5%) or no coronary rethrombosis and no hematological evidence of thrombin generation in these studies (PRIMI Trial Study Group, Lancet 1989, 1: 863-867; Weaver, J. Am. Coll. Cardiol., 1994, 241: 242-1248). Unfortunately, at therapeutic doses, proUK became vulnerable to spontaneous activation into the enzyme form, two-chain urokinase (tcUK), in plasma. Since tcUK is a non-fibrin-specific activator, it causes plasminemia, which is associated with a significant bleeding risk. For this reason, marketing approval was denied and proUK development was abandoned in the West. However, research continues and proUK can be used in some therapeutic methods that inhibit the activation into tcUK.

The instability of proUK in plasma relates to its relatively high intrinsic catalytic activity. Structure-function studies revealed the charged residues in a flexible loop consisting of amino acid residues 297-313 in the catalytic domain are responsible for this activity. Mutagenesis in the flexible loop region resulted in modulation of the intrinsic activity of proUK. Exemplary proUK "flexible loop" mutants with reduced intrinsic catalytic activity are described in U.S. Pat. No. 5,472,692 (incorporated herein by reference in its entirety), such as Gly299→Ala mutant, Lys300→His mutant (known as "M5" or "M5 mutant"), Lys300→Ala mutant, and Glu301→His mutant.

One of these proUK "flexible loop" mutants, M5 (Lys300→His), has been tested both in vitro and in vivo, and was shown to dissolve blood clots much faster than native proUK (Liu et al., Circulation Research, 2002, 90:757-763). The intrinsic activity of the single-chain M5 mutant is five-fold lower than proUK, so M5 is more stable in blood than native proUK and less likely to spontaneously convert into active enzyme form and cause hemophilia-like side effects (Liu, Biochemistry, 1996, 35: 14070-14076). The activity of the two-chain enzymatic form of mproUKs, e.g., M5, and the mode of action of mproUKs, e.g., M5, remain the same as native proUK (Sun, J. Biol. Chem., 1997, 272: 23818-23823; Liu, Circu. Res., 2002, 90: 757-763). mproUKs like M5 possess another superior property; they can be inhibited by endogenous plasma C1-inhibitor, providing protection against non-specific side effects without interfering with fibrinolysis by mproUK (Gurewich, J. Thrombos. Haemost., 2006, 4: 1559-1565; Pannell, J. Thromb. Haemost., 2007, 5: 1047-1054; Gurewich, Thromb. Haemost., 2009, 102: 279-286). Importantly, mproUKs such as M5 show much less hemorrhagic side effects normally associated with thrombolytic agents as described in U.S. Pat. No. 7,074,401 (incorporated herein by reference in its entirety). In addition, mproUKs such as M5 can be synthesized according to the methods described in U.S. Pat. No. 7,070,958 (incorporated herein by reference in its entirety).

M5 and other mproUKs are expected to be safe for human administration, because (1) they are essentially a natural human protein (99.8% similarity to native proUK), (2) they are free of antigenic (immunologic) reactions, and (3) naturally occurring human proUK and recombinant human proUK from E. coli have already been safely administered to about 5,000 human patients in Phase III clinical studies.

Combination Therapy of Mini-Dose tPA and Mini-Dose mproUK with a Minimal Waiting Period of at Least Ten Minutes In Vivo By utilizing the complementary mechanism of action of tPA and proUK or mproUK on fibrin-bound plasminogen action, and importantly, avoiding free tPA's inhibitory effect on mproUK lysis by waiting at least ten minutes after the administration of tPA to allow the added tPA to initiate fibrin degradation and then be cleared from the blood stream (tPA's half-life is about 5 minutes and so the waiting period should be at least two half-lives) before the mproUK is administered, the present inventor has demonstrated that maximum arterial patency rate is attained with a combination of a mini-dose of tPA plus an infusion of a mini-dose of mproUK, e.g., M5 (at 30 to 40% of monotherapy dose), to give a maximum arterial patency rate based on clot lysis data that is twice as fast as prior combinations of tPA and proUK administered in combination without the minimum waiting period of at least ten minutes.

In particular, as shown in the Examples and in Table 1 below, the data shows a mean time to reach 50% clot lysis of about 65 minutes (mean) using the new sequential methods with a waiting period, compared to about 107 minutes (mean) using sequential administration.

Mutant proUK such as M5 is used instead of native proUK, because mproUK is more stable in plasma and remains in its proenzyme form while native proUK tends to spontaneously convert into urokinase and cause hemophiliac-like side effects. Thus, the maximum clot lysis rate can be achieved by the tPA-mproUK combination with only a fraction of the monotherapy doses of tPA and mproUK.

Clinically, the tPA-waiting period-mproUK sequential combination therapy can be used to treat patients with stroke or heart attack symptoms promptly without the delay caused by time-consuming diagnostic procedures. This is possible because by this method because it is unlikely to be associated with any significant bleeding risk. Provided herein are methods of treating a subject, e.g., a human patient, with symptoms of a stroke or an acute myocardial infarction (AMI) more rapidly and more effectively with a higher than tPA TIMI-3 patency rate and with a far lower risk of bleeding complications. The methods include (a) identifying a subject who potentially had a stroke or AMI by observing one or more symptoms of a stroke or AMI without taking time to determine the cause of the stroke or AMI; (b) administering to the subject a mini-dose as an intravenous bolus, i.e., less than 5 mg of tissue plasminogen activator (tPA), e.g., 2.0, 2.5, 3.0, 3.5, 4.0, or 4.5 mg of tPA; (c) waiting at least ten minutes after completing the administration of the tPA; and (d) thereafter administering an intravenous infusion of a mini-dose of mutant proUK (mproUK) infused over 60 to 90 minutes, e.g., 60, 65, 70, 75, 80, 85, or 90 minutes, at a dosage rate of 20 to 50 mg/hour, e.g., 20 to 40 mg/hour, e.g., 25, 30, 35, 40, or 45 mg/hour; wherein a higher than previously possible arterial patency rate is achieved with minimal associated hemorrhagic side effects due to the lower doses made possible by this regimen.

The methods described herein can be used to treat stroke, which can be ischemic or hemorrhagic. Ischemic stroke is caused by a thrombus obstructing blood flow, while hemorrhagic stroke is caused by a broken blood vessel. While the hemorrhagic stroke cannot be helped by the treatment, the important point is that the new methods will do no harm. About 85% of the time, a stroke is ischemic, e.g., caused by a blood clot, and is therefore amenable to treatment by a thrombolytic agent. The timing of reperfusion after an ischemic stroke is critical, because the longer the brain cells are without oxygenated blood, the more brain cells are irretrievably lost. However, it is difficult and time consuming to fully establish the cause of a stroke, yet an accurate diagnosis is critical for treatment with currently available thrombolytic agents due to the high risk of hemorrhagic side effects. Administering a thrombolytic agent to an ischemic stroke patient is the proper therapy, but even when a thrombotic cause is established, the tPA treatment is associated with a 7% risk of inducing an intracranial hemorrhage. When current thrombolytic agents are administered to a hemorrhagic stroke, due to diagnostic error, there is a high risk of killing the patient. Although it takes time to establish and confirm the actual cause of a stroke, the clinical diagnosis is usually straightforward and is based on visual observations of the basic symptoms of stroke exhibited by a person (such as sudden onset of one-sided paralysis). These symptoms can be readily determined by one skilled in the medical field, such as an Emergency Medical Technician (EMT), a nurse, or a doctor, or even a layperson with minimal training. Therefore, sufficiently safe treatment according to the methods described herein can be initiated early.

A subject with symptoms of stroke can be treated promptly using the methods described herein by administration of a bolus of a mini-dose of tPA followed by an infusion of mini-dose mproUK. The very low dose of tPA administered as a single bolus (it is currently given as a high-dose long infusion) minimizes potential hemorrhagic risk, since any unbound tPA is rapidly cleared and/or irreversibly inhibited. Since the sequential combination with pause can lyse a thrombus, and also spare hemostatic fibrin, the combination can be used to treat patients on clinical diagnosis of a stroke without incurring the risk of aggravating bleeding in the brain in case the cause is not a thrombus. Thus, it is possible to initiate treatment without delay, thereby maximizing salvage of brain function and mortality reduction. To make this possible, treatment must be administered promptly prior to hospitalization.

The methods described herein can also be used to treat heart attack, e.g., acute myocardial infarction. A heart attack occurs when one of the coronary arteries is blocked, e.g., by a blood clot. The timing of reperfusion after a heart attack is critical, because the longer the heart muscle is without oxygenated blood, the more muscle cells are damaged or lost. The present treatment of choice is by catheterization and angioplasty, which requires hospitalization, an available catheterization room and staff at the ready. This delays treatment by several hours and carries a high cost. This first one hour after a coronary occlusion has been called the "Golden Hour," because it is the time during which the maximum salvage of heart muscle and the maximum reduction in mortality is possible. Pretreatment with tPA to gain time before catheterization has been generally abandoned since multiple studies have shown that tPA significantly increase the complication rate of angioplasty. As a result, tPA has been deemed incompatible with angioplasty, and full dose tPA for this purpose is no longer used, neither is any other thrombolytic.

A subject with symptoms of a heart attack can be treated by administration of a bolus of a low dose of tPA followed by an infusion of an mproUK such as M5 as described herein. It has been well established that proUK is not associated with the side effects of tPA that made it incompatible with angioplasty. Therefore, the sequential combination with the delay can be used as first line treatment prior to angioplasty, if this procedure is still needed.

C1-Inhibitor

C1-inhibitor is a 104 KD serine protease inhibitor with a normal plasma concentration of about 250 µg/ml and a half-life of about 28 hours. Deficiency of this protein has been associated with a disease called hereditary angioedema. C1-inhibitor has long been administered clinically for the treatment of hereditary angioedema. Commercially available C1-inhibitors include CINRYZE®, CETOR®, BERINERT®, and RUCONEST®.

The active enzymes two-chain UK or mUK generated during fibrinolysis are eventually released into the plasma where plasminogen activation becomes a liability. Quenching this activity requires plasma inhibitors. As described in U.S. Pat. No. 7,837,992 (incorporated herein by reference), an inhibitor complex of C1-inhibitor appeared within minutes of the incubation of enzyme mUK with human or dog plasma. C1-inhibitor is present endogenously in human body and can be supplemented pharmacologically. The endogenous C1-inhibitor was shown to be very effective in quenching activity of mUK, e.g., tcM5, but not UK activity (Gurewich, J. Thrombos. Haemost., 2006; 4: 1559-1565; Pannell, J. Thromb. Haemost., 2007; 5: 1047-1054; Gurewich, Thromb. Haemost., 2009; 102: 279-286). As shown in U.S. Pat. No. 7,837,992, the C1-inhibitor by inhibiting mUK effectively stabilized the mproUK like M5 in plasma and allowed a higher concentration of mproUK like M5 to be tolerated without compromising fibrin-specificity.

The methods of treating a subject with symptoms of stroke or acute myocardial infarction disclosed herein can further include administration of a third composition comprising a C1-inhibitor to the subject. The C1-inhibitor can be administered as a bolus in an amount sufficient to establish a concentration of C1-inhibitor in the subject's plasma that is within the range of two to three times above normal physiological level of C1-inhibitor (about 250 µg/ml), i.e., about 500-750 µg/ml. For example, the third composition can include 500-1500 mg of C1-inhibitor. In some embodiments, the third composition can be administered to the subject before the administration of the second composition. In some embodiments, the third composition can be administered to the subject simultaneously with the second composition.

Pharmaceutical Compositions, Dosage Regimens, and Methods of Administration

Pharmaceutical compositions provided herein can include specific dosages of tPA and a proUK or proUK mutant such as M5 as active ingredients. The active ingredient of a pharmaceutical composition, e.g., tPA or mproUK, can be formulated for delivery by intravenous injections.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, N.Y.). For example, solutions or suspensions used for parenteral administration can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfate; chelating agents such as ethylenediaminetetraacetic acid EDTA); buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injection can include sterile aqueous solutions (where water-soluble), dispersions, and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, the composition must be sterile and should be fluid to the extent that easy syringeability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

The pharmaceutical compositions can be included in a container, pack, or dispenser together with instructions for administration.

Dosage regimens can be adjusted to provide the optimum therapeutic response. See e.g., Physicians' Desk Reference, 63rd edition, Thomson Reuters, Nov. 30, 2008. For example, Dosage, toxicity, and therapeutic efficacy of the therapeutic compounds within the ranges defined herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index, which can be expressed as the ratio LD50/ED50. Compounds that exhibit high therapeutic indices are preferred.

The tPA bolus can include 2-5 mg of tPA, e.g., about 2 mg, about 2.5 mg, about 3 mg, about 3.5 mg, about 4 mg, about 4.5 mg, or about 5 mg. The intravenous dose of mproUK, e.g., M5, should be 20-50 mg/hour (e.g., 20-40, 25, 30, 35, 40, or 45 mg/hour mg/hour) for 60, 65, 70, 75, 80, 85, or 90 minutes. The C1-inhibitor can be administered if necessary as a bolus in an amount sufficient to establish a concentration of C1-inhibitor in the subject's plasma that is about 500 µg/ml. For example, the C1-inhibitor bolus can include 500-1500 mg of C1-inhibitor.

For patients with stroke or acute myocardial infarction, the time needed to reperfusion is critical to recovery of function and survival. These findings suggest that a combination of a mini-dose bolus of tPA and M5 infusion can achieve therapeutic thrombolysis in a safer and more effective way. Thus, patients with stroke or acute myocardial infarction can be treated promptly with a sequential combination with delay of tPA and M5.

Figure 4:
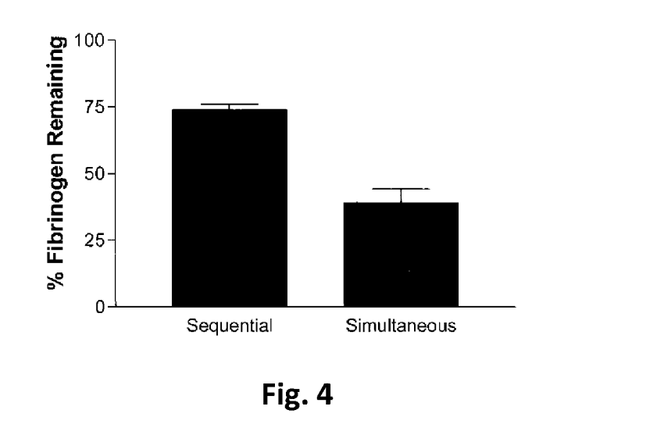
FIG. 4 is a bar graph that shows fibrinogen degradation (percent of fibrinogen remaining) associated with sequential vs. simultaneous clot lysis, expressed as a percent of the baseline fibrinogen concentration at the end of clot lysis (mean and SD shown). There was significantly ($p<0.01$) less fibrinogenolysis (fibrinogen degradation) with sequential clot lysis (about 37% vs almost 75%), which at the same time induced a more rapid rate of clot lysis.

Efficacy of thrombolysis is defined by the TIMI-3 patency rate, which has been correlated with the best recovery of function and mortality reduction. This TIMI-3 endpoint, however, has always had to be significantly compromised by the hemorrhagic complication rate. This problem has mandated a strict upper dose limit, so that maximal thrombolytic efficacy has always been precluded. With the sequential tPA, M5 combination, as described, optimal lysis can be achieved for the first time, since it can obtained with a lower, rather than higher activator dose. As a result, the associated risk of bleeding is reduced instead of increased (see FIG. 4 showing less fibrinogen degradation with sequential lysis according to the new methods described herein).

By using this new thrombolytic regimen for therapy, an optimal rate of TIMI-3 patency can be achieved for the first time, since it has always been precluded by the unacceptably high bleeding risk associated with this rate. This also means that an unprecedented reduction in mortality and morbidity from AMI and stroke is made possible. This can be anticipated with confidence based on well-established benefit of early TIMI-3 reperfusion.

Kits

Also provided herein are kits that include at least a composition comprising tissue plasminogen activator (tPA) in one container and another composition comprising a proUK, e.g., a mutant proUK such as M5, in a separate container. The kits are used to carry out the therapeutic methods described herein. The first composition can be formulated suitable for administration as a bolus, and can include 2-5 mg of tPA. The second composition can be formulated suitable for intravenous infusion. The second composition can include 20-50 mg (e.g., 25, 30, 35, 40, or 45 mg) of the mproUK, for infusion over a period of 60 minutes or additional mproUK for an additional 30 minutes of infusion (at the same rate of 20-50, e.g., 20-40 or 20-30 mg/hour). The kit can also include a third composition comprising C1-inhibitor. The third composition can be formulated for bolus administration, and can include about 500-1500 mg of C1-inhibitor.

Kits generally include the following major elements: packaging, reagents comprising binding compositions as described above, optionally a control, and instructions. Packaging can be a box-like structure for holding a vial (or number of vials) containing the compositions, and instructions for use in a method described herein. Individuals skilled in the art can readily modify the packaging to suit individual needs.

Compositions and kits provided herein can be used in accordance with any of the methods (e.g., treatment methods) described above. For example, compositions and kits containing a composition comprising tPA and another composition comprising a proUK mutant, e.g., the M5 mutant, can be used to treat stroke, heart attack, or other cardiovascular diseases caused by a thrombus such as peripheral gangrene. Those skilled in the art will be aware of other suitable uses for compositions and kits provided herein, and will be able to employ the compositions and kits for such uses.

EXAMPLES

The following examples further describe the invention and disclosure herein, and do not limit the scope of the inventions described in the claims.

Example 1—Clot Lysis Studies

The automated clot lysis assay used for other plasminogen activators cannot be used in studies of proUK due to its sensitivity to thrombin and plasmin. When used, thrombin inactivates some of the proUK, and whatever remains will then be converted to two-chain proUK (tc-proUK) during the lytic phase of the assay. Therefore, a 24 hour-old preformed clot incubated at 37° in plasma was used. A plasma milieu is essential not only to approximate in vivo lysis, but more importantly, because without inhibitors, the intrinsic activity of proUK activates plasminogen non-specifically and plasmin in turn converts proUK to tc-proUK.

Mutant proUK was produced in *E. coli* by PxTherapeutics (Grenoble, France). Single-chain tPA was a product (Cath-Flo®) produced by Genentech (South San Francisco, Calif.). Human fibrinogen for labeling was from Kabi Grade L (Chromogenix, Milan, Italy). Aprotinin, fluorescein isothiocyanate, bovine thrombin, and thromboplastin (ThromboMax®) were from Sigma Chemicals, St. Louis, Mo. Human plasma was obtained from the blood bank of Mount Auburn Hospital, Cambridge, Mass.

Clots were made up from 0.2 ml pooled blood bank plasma in glass tubes by recalcification (to 35 mM) with the addition of a trace of thromboplastin and a tracer of fluoresceinated fibrinogen [11]. The clots were then incubated at 37° C. for 1 hour and overnight at room temperature. The following day, the clots were placed into 2 ml of pooled bank plasma to which the activators were previously added as specified.

For the sequential exposure, a clot was placed in 2 mL plasma containing tPA (0.2 µg/mL) for 5 minutes, followed by a single wash in 4 mL of plasma to remove unbound tPA. The washing step took about 10 to 15 minutes, which correlates to the waiting period of at least 10 minutes in vivo as recited herein.

Figure 1:
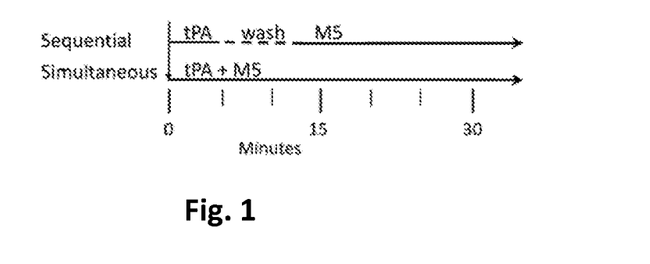
FIG. 1 represents a time line of the two different clot lysis conditions used in the examples described herein.

Then the clot was transferred to 2 ml of plasma enriched with mproUK (6 µg/ml) and incubated at 37° C. For simultaneous lysis, the clots were incubated in 2 mL of plasma containing both activators at the same concentrations. A time-line of the two conditions is shown in FIG. 1.

Clot lysis was monitored by taking 50 µL samples at time points for reading of fluorescence, representing fibrin degradation products released from the clots (Fluoroskan® Ascent CF fluorescent plate reader).

Lysis curves were plotted as a percent clot lysis over time as calculated from the fluorescent measurements at the end of a complete lysis with correction for the natural fluorescence of plasma. The time to 50% lysis under each of the experimental conditions was determined from the lysis graphs and was used as the principal endpoint.

Figure 2:
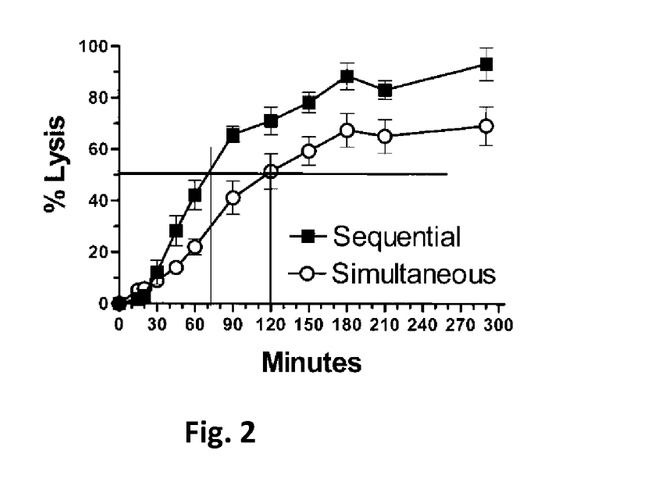
FIG. 2 is a graph showing results from a representative clot lysis experiment that compares the sequential exposure of clots to tPA (0.2 µg/ml) followed by a wash step that removes the unbound (not fibrin-bound) tPA (about 80% of it) and then incubation of the clot with M5 (6 µg/ml). This was compared with the simultaneous exposure of clots to the full concentrations of both activators together. The graph shows mean and standard deviation (SD) from sextuplicate lysis curves under the two conditions shown (sequential with a minimum waiting period and simultaneous). The mean 50% lysis times, which is the current standard for this assay due to the asymptotic nature of the curves making the 100% point difficult to determine, were 72 and 120 minutes for the sequential and simultaneous conditions, respectively. Therefore, sequential clot lysis was almost twice as rapid, despite having far less (~20%) tPA and undergoing about a 15 minute delay due to the wash procedure.

Each of the clot lysis experiments comparing the two conditions was done in sextuplicate in five experiments and quadruplicate in one. The results are shown in Table 1 and in FIG. 2 (sequential ■, simultaneous ○). We used Graph Pad Prism for preparing the graphs and for statistical analysis (means, standard deviations, and Student's T test).

As shown in Table 1 below, which shows the time to reach fifty percent clot lysis as determined from all experiments comparing the two conditions, the mean 50% clot lysis time was 65 minutes for the sequential administration with a washing step (which corresponds to an in vivo waiting period or at least ten minutes), and 107 minutes for the simultaneous administration ($P<0.0001$). The sequential lysis was almost invariably shorter, and never longer, in all of the individual experiments, and overall was almost twice as fast.

TABLE 1

50% Clot Lysis Times

| Exp. | Sequential | Simultaneous | Replicate |
|---|---|---|---|
| 1. | 55 | 95 | ×6 |
| 2. | 32 | 60 | ×6 |
| 3. | 80 | 140 | ×6 |
| 4. | 70 | 109 | ×4 |
| 5. | 70 | 115 | ×6 |
| 6. | 85 | 124 | ×6 |
| Mean | 65 | 107 | |
| SD | 17 | 25 | |

($p < 0.0001$)

Figure 3:
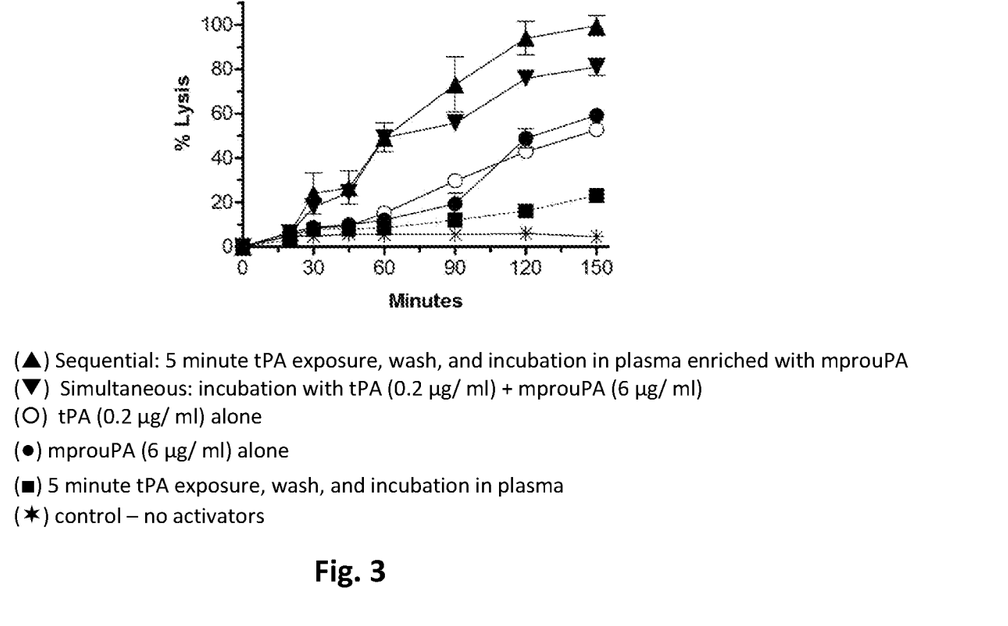
FIG. 3 is a graph showing clot lysis under the various conditions and with different components to show that a far lower dose of tPA was involved in the sequential lysis. This graph shows: control lysis of clots in plasma (*); lysis of clots after a 5 minute tPA exposure and a wash step of at least ten minutes (■); lysis of clots by mproUK (●) or tPA alone (○); lysis by the washed clots (■) when added to plasma containing mproUK (▲) and of clots lysed by tPA and mproUK in plasma (▼). The mean results of 34 individual experiments were 65 minutes and 107 minutes ($p<0.0001$) for the sequential and simultaneous 50% lysis times, respectively. As in FIG. 2, the washed clots containing a much lower amount of tPA induced superior lysis.

To evaluate the relative lytic contribution of lysis by the tPA remaining bound to the clot after the wash, and of the tPA and proUK in plasma alone, they were tested separately. These experiments were done in triplicate and the results are shown in FIG. 3, which shows that clot lysis in the plasma milieu induced by mproUK (6 µg/mL) (●) or tPA (0.2 µg/mL) (○) alone was comparable. The shapes of the graphs differed in that mproUK showed a prolonged lag phase at the outset, which is characteristic and due to its dependence on plasminogen on degraded rather than intact fibrin. By contrast, lysis of clots after the wash step to remove unbound tPA (which corresponds to the waiting period of at least ten minutes in vivo), reached only 20% (■), indicating that the bulk of the tPA had washed off. This was reflected by the much more effective clot lysis seen with the total amount of tPA, which reached 50% (○).

As shown in FIG. 3, when tPA was incubated in plasma enriched with mproUK, the step-wise combination including a 10-15-minute washing step induced significantly more rapid lysis (▲) than when the tPA and proUK were administered simultaneously (▼). This occurred despite the simultaneous combination containing five time more tPA (100% vs. 20%), none of it having been washed off, and not being interrupted by the wash procedure.

This paradoxical finding suggested that the additional tPA in plasma acted as a competitive inhibitor of lysis of mproUK clot lysis. Therefore, the present findings indicate that the previous showing of a synergistic effect between tPA and proUK can be surprisingly enhanced almost two-fold when the combination is a sequential one and tPA clot contact is limited to five minutes followed by a wash step that removes the unbound tPA. In vivo, after the tPA bolus is administered, the tPA that is unbound to fibrin is cleared from the circulation rapidly (T½~5 min) and inhibited by plasma inhibitors. This fibrinolytic paradigm holds promise for better therapeutic thrombolysis for both stroke and AMI.

Example 2—Fibrinogen Determination

After completion of clot lysis, a final plasma sample (1.0 mL) was obtained for determination of fibrinogen. Further proteolysis was prevented by the addition of aprotinin (200 KIU/mL) to the sample.

Fibrinogen was measured as thrombin-clottable protein. After dilution of the plasma sample with 1 ml phosphate-buffered saline, 1 mL bovine thrombin (100 NIH units/mL) was added, mixed gently, and incubated for 2 hours at 37° C. The formed clots were wound onto a thin, long stemmed plastic transfer pipette tip to which the gel adhered, and the serum content was expressed by pressure against the test tube wall and then gently against a paper towel. The white-appearing fibrin on the pipette stem was then placed in 5 mL of saline for >1 h to allow diffusion of any remaining serum proteins. The fibrin was peeled off the tip and placed into 1 mL of 5% NaOH, boiled for 1 minute, and then kept at room temp until all fibrin had gone into solution. The protein in the solution was measured spectrophotometrically at 280 nm. The results were recorded as percent of the baseline (BL) fibrinogen obtained from a control plasma sample.

As shown in FIG. 4, fibrinogen concentrations in plasma at the end of lysis showed about 25% loss of fibrinogen under sequential conditions compared with about 60% loss under simultaneous conditions, a significant ($p<0.01$) difference. Therefore, there was almost twice as much fibrinogen degradation associated with simultaneous clot lysis ($p<0.01$), even though it was less effective, indicating that sequential clot lysis was both more effective and caused fewer of the side effects responsible for bleeding complications than simultaneous clot lysis. This is contrary to the typical expectations that more effective fibrinolysis invariably requires higher doses of the activator, which also means a higher incidence of side effects. These findings also further support the finding noted above that the tPA in the simultaneous combination acted like an inhibitor of mproUK clot lysis.

Example 4—Clinical Trials

Clinical human trials begin with Phase 1 testing of the new dosing regimen in normal subjects. The subjects received a mini bolus of 5 mg of tPA, followed by a waiting period of 10 minutes, and then followed by an infusion of mutant proUK for 60 and 90 minutes at a dose of 40 mg/hour.

In particular, healthy male volunteers enrolled were between the ages of 18 and 35 years (inclusive), ≥60 kg in body weight, and with body mass index of 18.5 to 30 kg/m2 (inclusive). Subjects had normal values in assays for α2-antiplasmin (>75%) and fibrinogen (2.1-3.8 g/L); negative serology for human immunodeficiency, hepatitis B, and hepatitis C viruses; and negative testing for alcohol and drug use. Subjects were excluded if there was likelihood of developing a clinically significant bleeding event due to diseases associated with bleeding tendency, clinical history, or participation in high impact sports activities within 2 weeks of dosing; and if they smoked tobacco within 3 months or ever smoked >5 cigarettes/day.

On day 1, drugs administered were M5 ("HisproUK" from Thrombolytic Science, LLC, Cambridge, Mass.), tPA (Alteplase, Actilyse®, Boehringer Ingelheim International, Rhein, Germany), or respective matching placebo. Doses of HisproUK for infusion were based on previous preclinical and clinical experience with HisproUK and proUK, respectively. Dose escalation occurred only after review by the safety committee of post-treatment levels of fibrinogen, α2-antiplasmin, C-reactive protein, and cytokines. When subjects received both drugs, the same intravenous access site was used, flushing the cannula with 0.9% NaCl between treatments. There was either a 10-minute window between tPA and HisproUK administration or HisproUK was administered immediately following tPA.

All HisproUK administration was double-blind. tPA monotherapy was double-blinded, but tPA therapy that preceded treatment with HisproUK was given to all subjects in the cohort and was not blinded. Primary endpoints were the maximum degrees of fibrinogen degradation, α2-antiplasmin decrease, and plasminogen consumption; the nature, frequency, and severity of adverse events (AEs); and changes in plasma concentrations of cytokines and in vital signs, laboratory results, or ECG-findings.

Changes in concentrations of plasma factors (fibrinogen, α2-antiplasmin, plasminogen, IL-6, IL-8, and TNFα) were analyzed using repeated measures with a mixed analysis of variance model. Fixed factors were treatment, time, and treatment by time; the random factor was subject; and the covariate was the prevalue of the dosing day. Data were back-transformed from the natural log for presentation. Planned comparisons included those between placebo and each of the other cohorts and between tPA alone and tPA+HisproUK. Statistical analysis was performed using SAS 9.1.3 for Windows (SAS Institute Inc., Cary, N.C.).

Plasmin generation was assessed indirectly by two biochemical measures, α2-antiplasmin consumption and plasminogen depletion. Plasma α2-antiplasmin levels were significantly reduced compared with placebo in patients receiving HisproUK 50 mg, HisproUK 65 mg, tPA 5 mg, and sequential tPA 5 mg followed by HisproUK 40 mg (Table 2). Compared with tPA 5 mg alone, neither combination treatment was significantly different in α2-antiplasmin concentration. Of note, substantial levels of α2-antiplasmin remained after each of the treatments (data not shown).

Plasminogen levels also decreased in some cohorts. Plasminogen reduction was significantly greater with the HisproUK 50 mg group compared with placebo (Table 2).

TABLE 2

Summary of Repeated Measures Analysis

| LSM Changes from Baseline | Placebo | HisproUK 20 mg | HisproUK 50 mg | HisproUK 65 mg | tPA 5 mg | tPA 5 mg + HisproUK 20 mg | tPA 5 mg + HisproUK 40 mg |
|---|---|---|---|---|---|---|---|
| Fibrinogen (g/L) | 0.092 | 0.324*** | 0.021 | 0.250 | −0.003 | 0.206 | −0.034 |
| α2-antiplasmin (%) | 4.0 | −6.2 | −25.8* | −25.0*** | −14.5** | −2.3 | −26.4*** |
| Plasminogen (%) | 4.9 | −6.9 | −25.3** | −15.4 | 2.1 | −9.2 | NA |

*P vs. placebo < 0.001,
**P vs. placebo < 0.01,
***P vs. placebo < 0.05
HisproUK, mutant prourokinase;
tPA, tissue plasminogen activator;
NA, not available;
LSM, least squares method Neither the sequential treatment regimens nor the monotherapies revealed any serious safety signals, as there were no deaths or serious adverse events (AEs) and no clinically relevant changes in vital signs or ECG readings. Among the 15 subjects who received HisproUK, the most common AEs were mild gastrointestinal (GI) events: abdominal discomfort (n=1), diarrhea (n=5), nausea (n=5), and vomiting (n=3). AEs of moderate severity were infrequent. Only one GI AE of moderate severity occurred, nausea in a patient who received HisproUK 50 mg. This patient also experienced moderate pyrexia. As mentioned above, another patient who received HisproUK 50 mg experienced a moderately severe decrease in blood fibrinogen. A third patient, receiving HisproUK 65 mg, experienced moderately severe syncopy. All AEs were temporary and resolved within periods of 30 minutes to overnight.

It is noteworthy that in the present investigation, the low dose 5 mg bolus of tPA administered prior to the HisproUK infusion did not negatively affect the hemostatic parameter fibrinogen (Table 2). Efficacy was examined in this trial by two indirect measures of plasmin generation. Significant decreases in α2-antiplasmin suggest that tPA 5 mg monotherapy and the higher doses of HisproUK, with and without tPA, increased plasmin production compared with placebo. No significant differences were seen in indices of plasmin production between the sequential dual treatment regimens and tPA 5 mg monotherapy using either assay. Thus, the mutant plasminogen activator HisproUK and the sequential administration of tPA and HisproUK showed signs of plasmin generation in healthy men without interference of normal hemostasis.

The next phase of the clinical trials will include testing the new dosing regimen in at least 50 stroke patients. The protocol is simple. Patients with symptoms and signs consistent with stroke are treated as soon as possible after the start of symptoms, e.g., in an ambulance or doctor's office or in the hospital emergency room with an intravenous bolus infusion of 4 mg of tPA over no more than 30 seconds. After a waiting period of 10 minutes after the end of the tPA infusion, administer an infusion of M5 at a rate of 40 mg/h for 90 minutes.

Thereafter, each patient undergoes an angiogram and endovascular procedure, e.g., thrombectomy, to determine whether the patient still has any blood clot present, and any remaining clots are removed and/or a TIMI arterial patency score is determined.

REFERENCES

1. Voskuilen M, Vermond A, Veeneman G H, van Boom J H, Klasen E A, Zegers N D, Nieuwenhuizen W. Fibrinogen lysine residue Aα157 plays a crucial role in the fibrin-induced acceleration of plasminogen activation, catalyzed by tissue-type plasminogen activator. J Biol Chem 1987; 262(13); 5944-5946.
2. Hoylaerts M, Rijken D C, Lijnen H R, Collen D. Kinetics of the activation of plasminogen by human tissue plasminogen activator. Role of fibrin. J Biol Chem 1982; 257: 2912-2919.
3. Liu J, Gurewich V. Fragment E-2 from fibrin substantially enhances pro-urokinase-induced glu-plasminogen activation. A kinetic study using a plasmin-resistant mutant pro-urokinase (Ala-158-rproUK). Biochemistry 1992; 31:6311-6317.
4. Liu J, Gurewich V. A comparative study of the promotion of tissue plasminogen activator and pro-urokinase-induced plasminogen activation by fragments D and E-2 of fibrin. J Clin Invest 1991; 88:2012-2017.
5. Petersen L C. Kinetics of reciprocal pro-urokinase/plasminogen activation. Stimulation by a template formed by the urokinase receptor bound to poly (D-lysine). Eur J Biochem 1997; 245:316-323.
6. Pannell R, Black J, Gurewich V. The complementary modes of action of tissue plasminogen activator (t-PA) and pro-urokinase (pro-UK) by which their synergistic effect on clot lysis may be explained. J Clin Invest 1988; 81:853-859.
7. Gurewich V, Pannell R. Synergism of tissue-type plasminogen activator (t-PA) and single-chain urokinase-type plasminogen activator (scu-PA) on clot lysis in vitro and a mechanism for this effect. Thromb Haemost 1987; 57:372-378.
8. Liu J N, Tang W, Sun Z Y, Kung W, Pannell R, Sarmientos P, Gurewich V. A site-directed mutagenesis of pro-urokinase which substantially reduces its intrinsic activity. Biochemistry 1996; 35:14070-14076.
9. Liu J N, Liu J X, Liu B, Sun Z, Zuo J L, Zhang P, Zhang J, Chen Y, Gurewich V. A prourokinase mutant which induces highly effective clot lysis without interfering with hemostasis. Circu Res. 2002; 90:757-763.
10. Pannell R, Li S, Gurewich V. Highly effective fibrinolysis by a sequential synergistic combination of mini-dose tPA plus low-dose mutant proUK. PLOS One 2015; 10:1-15.
11. Dmitry V, Sakharov J, Nagelkerke F, Dingeman C, Rijken D C. Rearrangements of the fibrin network and spatial distribution of fibrinolytic components during plasma clot lysis. J Biol Chem 1996; 271: 2133-2138.
12. Suenson E, Lützen O, Thorsen S. Initial plasmin-degradation of fibrin as the basis of a positive feed-back mechanism in fibrinolysis. Eur J Biochem 1984; 140: 513-522.

13. Harpel P C, Chang T S, Verderber E. Tissue plasminogen activator and urokinase mediate the binding of Glu-plasminogen to plasma fibrin I. Evidence for new binding sites in plasmin-degraded fibrin I. J Biol Chem 1985; 260(7):4432 (abstr).
14. Gurewich V. Therapeutic fibrinolysis. How efficacy and safety can be improved. J Am Coll Cardiol 2016; 68:2099-2106.
15. Liu J, Pannell R, Gurewich V. A transitional state of pro-urokinase which has a higher catalytic efficiency against glu-plasminogen than urokinase. J Biol Chem 1992; 267:15289-15292.
16. Baglin T P, Landown R, Frasson R, Huntington J A. Discovery and characterization of an antibody directed against exosite 1 of thrombin. J Thrommb Haemos 2016; 14:137-142.
17. Bugge T H, Flick M J, Danton M J S, Daugherty C C, Rømer J, Danø K, Carmeliet P, Collen D, Degen J L. Urokinase-type plasminogen activator is effective in fibrin clearance in the absence of its receptor or tissue-type plasminogen activator. Proc Natl Acad Sci USA 1996; 93:5899-5904.
18. Singh I, Burnand K G, Collins M, Luttun A, Collen D, Boelhouwer B, Smith A. Failure of thrombus to resolve in urokinase-type plasminogen activator gene-knockout mice: rescue by normal bone marrow-derived cells. Circulation 2003; 107:869-875.
19. Pannell R, Gurewich V. A comparison of the rates of clot lysis in a plasma milieu induced by tissue plasminogen activator (t-PA) and rec-prourokinase: evidence that t-PA has a more restricted mode of action. Fibrinolysis 1992; 6:1-5.
20. Vaughan D E, Vautloutle E, Collen D. Urokinase binds to platelets through a specific saturable, low affinity mechanism. Fibrinolysis 1990; 4:141.
21. Gurewich V, Johnstone M T, Pannell R. The selective uptake of high molecular weight urokinase-type plasminogen activator by human platelets. Fibrinolysis 1995; 9:188-195.
22. Grau E, Moroz L A. Fibrinolytic activity of normal human blood monocytes. Thromb Res 1989; 53:145-162.
23. Zarich S W, Kowalchuk G J, Weaver W D, Loscalzo J, Sassower M, Manzo K, Byrnes C, Muller J E, Gurewich V for the PATENT Study Group. Sequential combination thrombolytic therapy for acute myocardial infarction: results of the pro-urokinase and t-PA enhancement of thrombolysis (PATENT) trial. J Am Coll Cardio 1995; 26:374-379.
24. Ross A M for the GUSTO Angiographic Investigators. The effects of tissue plasminogen activator, streptokinase, or both on coronary-artery patency, ventricular function, and survival after acute myocardial infarction. N Engl J Med 1993; 329:1615-1622.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject with symptoms of a stroke or an acute myocardial infarction (AMI) at a maximum arterial patency rate with minimal associated hemorrhagic side effects, the method comprising:

(a) identifying a subject who potentially had a stroke or AMI by observing one or more symptoms of a stroke or AMI without taking time to determine the cause of the stroke or AMI;
(b) administering to the subject a mini-dose of less than 5 mg of tissue plasminogen activator (tPA);
(c) waiting at least ten minutes after completing the administration of the tPA; and
(d) thereafter administering an intravenous infusion of a mini-dose of mutant proUK (mproUK), infused over 45 to 90 minutes, at a dosage rate of 20 to 50 mg/hour;
wherein a maximum arterial patency is achieved with minimal associated hemorrhagic side effects.

2. The method of claim 1, wherein the mini-dose of tPA is a bolus of 2.0 to 4.5 mg of tPA.

3. The method of claim 1, wherein the mutant proUK comprises a substitution of histidine for lysine at amino acid position 300 (Lys300→His) of human proUK.

4. The method of claim 1, wherein the subject has symptoms of a stroke.

5. The method of claim 1, wherein the minimal associated hemorrhagic side effects are determined as a level of fibrinogen degradation in the subject's blood of less than about 30 percent.

6. The method of claim 1, wherein the maximum arterial patency rate is indicated as having been achieved by a Thrombolysis In Myocardial Infarction (TIMI) score of 3.

7. The method of claim 2, wherein the bolus comprises 2.0 to 4.0 mg of tPA.

8. The method of claim 1, wherein the mproUK is administered as an intravenous infusion at a rate of 20-40 mg/hour for 45-90 minutes.

9. The method of claim 8, wherein the mproUK is administered as an intravenous infusion at a rate of 20-30 mg/hour for 45-60 minutes.

10. The method of claim 1, wherein the administration of the mproUK begins after a waiting period of at least 15 minutes after the administration of the tPA.

11. The method of claim 1, further comprising administering to the subject a bolus of C1-inhibitor.

12. The method of claim 11, wherein the C1-inhibitor is administered to the subject before or at about the same time as the administration of the proUK.

13. The method of claim 11, wherein the C1-inhibitor is administered in an amount sufficient to establish a concentration of C1-inhibitor that is about 500-750 µg/ml in the subject's blood.

14. The method of claim 11, wherein the C1-inhibitor is administered as a bolus of 500-1500 mg of C1-inhibitor.

15. The method of claim 1, wherein the mini-dose of tPA is a bolus of 2.0 to 4.0 mg of tPA infused over no more than 30 seconds, and after waiting at least ten minutes after completing the administration of the tPA, the mproUK is administered as an intravenous infusion at a rate of 20-40 mg/hour for 60-90 minutes.

16. The method of claim 15, wherein the mutant proUK comprises a substitution of histidine for lysine at amino acid position 300 (Lys300→His) of human proUK.

17. The method of claim 16, wherein the mutant human proUK is naturally occurring human proUK or recombinant human proUK.

18. The method of claim 1, wherein the mini-dose of tPA is a bolus of 4.0 mg of tPA infused over no more than 30 seconds, and after waiting at least ten minutes after completing the administration of the tPA, the mproUK is administered as an intravenous infusion at a rate of 35-40 mg/hour for 80-90 minutes.

19. The method of claim 18, wherein the mproUK comprises a substitution of histidine for lysine at amino acid position 300 (Lys300→His) of human proUK.

20. The method of claim 19, wherein the mutant human proUK is naturally occurring human proUK or recombinant human proUK.

\* \* \* \* \*

UNITED STATES PATENT AND TRADEMARK OFFICE
CERTIFICATE OF CORRECTION

PATENT NO. : 11,154,596 B2
APPLICATION NO. : 16/622720
DATED : October 26, 2021
INVENTOR(S) : Victor Gurewich Page 1 of 1

It is certified that error appears in the above-identified patent and that said Letters Patent is hereby corrected as shown below:

On the Title Page

Column 2, (Other Publications), Line 5, delete "Cardiovacular" and insert -- Cardiovascular --, therefor.

In the Specification

Column 1, Line 10, Below "reference." delete "CLAIM OF PRIORITY
This application claims the benefit of U.S. Provisional Application Ser. No. 62/521,254 filed on Jun. 16, 2017. The entire contents of the foregoing application is incorporated herein by reference.".

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*